United States Patent
Centola et al.

(10) Patent No.: US 9,474,604 B2
(45) Date of Patent: Oct. 25, 2016

(54) HEARTVALVE IMPLANT

(71) Applicant: NVT AG, Muri (CH)

(72) Inventors: Marcos Centola, Hechingen (DE); Emilia Kawa, Hechingen (DE)

(73) Assignee: NVT AG, Muri (CH)

( * ) Notice: Subject to any disclaimer, the term of this patent is extended or adjusted under 35 U.S.C. 154(b) by 0 days.

(21) Appl. No.: 14/660,065

(22) Filed: Mar. 17, 2015

(65) Prior Publication Data

US 2015/0265402 A1  Sep. 24, 2015

(30) Foreign Application Priority Data

Mar. 18, 2014  (EP) .................................... 14160492

(51) Int. Cl.
*A61F 2/24* (2006.01)
*A61F 2/95* (2013.01)

(52) U.S. Cl.
CPC .......... *A61F 2/2418* (2013.01); *A61F 2/2436* (2013.01); *A61F 2002/9505* (2013.01); *A61F 2210/0014* (2013.01)

(58) Field of Classification Search
CPC .......... A61F 2/06; A61F 2/24; A61F 2/2418; A61F 2/2409; A61F 2/2445; A61F 2/2427; A61F 2/2412; A61F 2/246; A61F 2/2475; A61F 2/2436
USPC ........... 623/1.11, 1.15, 1.24, 1.26, 2.14, 2.18
See application file for complete search history.

(56) References Cited

U.S. PATENT DOCUMENTS

| | | | | |
|---|---|---|---|---|
| 5,843,167 A * | 12/1998 | Dwyer | ...................... | A61F 2/07 623/1.14 |
| 6,077,297 A * | 6/2000 | Robinson | .................. | A61F 2/07 623/1.11 |
| 6,908,481 B2 * | 6/2005 | Cribier | .................. | A61F 2/2412 623/2.11 |
| 7,025,780 B2 * | 4/2006 | Gabbay | ................. | A61F 2/2418 623/2.13 |
| 7,267,686 B2 * | 9/2007 | DiMatteo | .............. | A61F 2/2412 137/850 |
| 7,452,371 B2 * | 11/2008 | Pavcnik | ..................... | A61F 2/01 623/1.24 |
| 7,566,343 B2 * | 7/2009 | Jenson | .................. | A61F 2/2412 623/1.26 |
| 7,569,072 B2 * | 8/2009 | Berg | ..................... | A61F 2/2409 623/1.26 |

(Continued)

FOREIGN PATENT DOCUMENTS

WO  WO2011119914 A1  9/2011

OTHER PUBLICATIONS

European Search Report or EP Application No. 14160492.6 dated Sep. 2, 2014, 7 pages.

*Primary Examiner* — Alvin Stewart
(74) *Attorney, Agent, or Firm* — Reising Ethington P.C.

(57) ABSTRACT

The present invention relates to a prosthetic heart valve, the prosthetic heart valve comprising a generally tubular stent support and a valve structure. The stent support comprises multiple rows of diamond-shaped cell structures and crowns at its distal and proximal end, as well as three V-shaped openings which open towards the distal end of stent support.

12 Claims, 3 Drawing Sheets

(56) References Cited

U.S. PATENT DOCUMENTS

| | | | | |
|---|---|---|---|---|
| 7,682,390 B2* | 3/2010 | Seguin | A61B 17/072 623/1.26 |
| 7,717,952 B2* | 5/2010 | Case | A61F 2/2418 623/1.24 |
| 7,871,434 B2* | 1/2011 | Case | A61F 2/2418 623/1.24 |
| 8,092,520 B2* | 1/2012 | Quadri | A61F 2/2418 623/1.26 |
| 8,257,429 B2* | 9/2012 | Pavcnik | A61F 2/2418 623/1.24 |
| 8,303,648 B2* | 11/2012 | Grewe | A61F 2/2412 623/1.24 |
| 8,449,599 B2* | 5/2013 | Chau | A61F 2/2418 623/1.24 |
| 8,454,678 B2* | 6/2013 | Hiles | A61F 2/2418 623/1.24 |
| 2003/0023303 A1* | 1/2003 | Palmaz | A61F 2/2418 623/2.18 |
| 2005/0137697 A1* | 6/2005 | Salahieh | A61F 2/2418 623/2.11 |
| 2006/0149360 A1* | 7/2006 | Schwammenthal | A61F 2/2418 623/1.24 |
| 2006/0259137 A1* | 11/2006 | Artof | A61F 2/2418 623/2.18 |
| 2006/0276813 A1* | 12/2006 | Greenberg | A61F 2/2418 606/158 |
| 2007/0288087 A1* | 12/2007 | Fearnot | A61F 2/2418 623/1.24 |
| 2008/0071369 A1* | 3/2008 | Tuval | A61F 2/2418 623/2.38 |
| 2008/0097586 A1* | 4/2008 | Pavcnik | A61F 2/01 623/1.24 |
| 2008/0125853 A1* | 5/2008 | Bailey | A61F 2/2418 623/1.14 |
| 2008/0255661 A1* | 10/2008 | Straubinger | A61F 2/2427 623/2.36 |
| 2010/0131055 A1* | 5/2010 | Case | A61F 2/2418 623/2.17 |
| 2010/0298927 A1* | 11/2010 | Greenberg | A61F 2/2418 623/1.26 |
| 2011/0238159 A1* | 9/2011 | Guyenot | A61F 2/2418 623/1.26 |
| 2011/0264196 A1* | 10/2011 | Savage | A61F 2/2418 623/1.26 |
| 2011/0264202 A1 | 10/2011 | Murray, III | |
| 2011/0288634 A1* | 11/2011 | Tuval | A61F 2/2418 623/1.26 |
| 2012/0116498 A1* | 5/2012 | Chuter | A61F 2/2412 623/1.26 |
| 2014/0005767 A1 | 1/2014 | Glazier | |
| 2015/0297381 A1* | 10/2015 | Essinger | A61F 2/82 623/1.12 |

* cited by examiner

HEARTVALVE IMPLANT

CROSS REFERENCES TO RELATED APPLICATIONS

This application claims priority from European patent application EP14160492.6, filed on Mar. 18, 2014 in the English language. The entire content of this priority application is incorporated herein by reference.

RELEVANT FIELD

The present invention relates to a prosthetic heart valve for replacement of a native valve of a human body.

BACKGROUND

Heart valve replacement is necessary where the native heart valve is damaged, mal- or nonfunctioning. In the heart, cardiac valves maintain the unidirectional flow of blood by opening and closing depending on the difference in pressure on each side. As such, a heart valve can be affected by a range of diseases and can, therefore, require cardiac valve replacement. The valve can either become leaky, i.e. regurgitant or insufficient, in which case the aortic valve is incompetent and blood flows passively back to the heart in the wrong direction. Further, the valve can become partially shut, i.e. stenotic, in which case the valve fails to open fully, thereby obstructing blood flow out from the heart. The two conditions frequently co-exist.

Heart valve replacement traditionally requires median sternotomy and thus open heart surgery, which is a major impact on the patient to be treated: The sternum is sawed in half and after opening of the pericardium, the patient is placed on a cardiopulmonary bypass machine. Once the patient is on bypass, the patient's diseased aortic valve is removed and a mechanical or tissue valve is put in its place. Besides the physical stress associated with this operation, there is a risk of death or serious complications from open heart surgery, in particular depending on the health and age of the patient.

However, systems have been developed which allow percutaneous introduction and deployment of prosthetic heart valves, by means of which open heart surgeries can be avoided. The deployment of such heart valve prostheses can either be achieved retrograde, i.e. against normal blood flow, or antegrade, with blood flow.

For percutaneous valve replacements, various types and configurations of prosthetic heart valves are presently used, wherein the actual shape and configuration of any particular prosthetic heart valve is dependent, on the one hand, upon the valve being replaced. Generally, the prosthetic heart valve designs attempt to replicate the function of the valve being replaced and thus will regularly include valve leaflet-like structures used with either bioprosthesis, which are usually made from animal tissues, either animal heart valve tissue or animal pericardial tissue, and which are treated to prevent rejection and to prevent calcification, or mechanical heart valve prostheses, which are generally composed entirely of synthetic or non-biological materials. As such, the replacement valves may include a valved segment that is mounted in some manner within an (self-)expandable stent structure. There are two types of stents on which the valves structures are ordinarily mounted: self-expanding stents and balloon-expandable stents. To place such valves into a delivery apparatus and ultimately into a patient, the valve must first be collapsed or crimped to reduce its circumferential size.

When a collapsed prosthetic valve has reached the desired implant site in the patient, i.e. at or near the annulus of the patient's heart valve that is to be replaced by the prosthetic valve, the prosthetic valve is deployed or released from the delivery apparatus and expanded to full operating size. With balloon-expandable valves, generally the entire valve is released and subsequently expanded by an expandable balloon positioned within the valve stent. With self-expanding valves, the deployment systems regularly comprise a retractable sheath, upon withdrawing of which the stent automatically begins to expand.

For a fully functioning prosthetic heart valve it is crucial that all of its components fulfill their respective task: The valve, on the one hand, needs to be adequately attached to the stent support, since otherwise the valve is prone to failure, and valve failure, in the circulatory system, has significant consequences for the patient. On the other hand, the stent support needs to fully expand and, thus, guarantee the secure fixation within the heart vessels.

Accordingly, there is a constant need for improving the deployment systems and prosthetic heart valves that are currently available, facilitating the handling of the prosthetic valve when loaded onto the deployment system in order to deliver it to the valve that needs to be replaced, while simultaneously guaranteeing the smooth and easy release of the prosthetic heart valve in the heart vessel.

Thus, it is an object of the present invention to provide for a prosthetic heart valve that fulfills the requirements above and overcomes the drawbacks of the presently available heart valve prostheses.

SUMMARY OF THE INVENTION

According to the invention, this and other objects are solved by a prosthetic heart valve for replacement of a native valve of a patient, wherein the prosthetic heart valve comprises (i) an expandable generally tubular stent support forming a wire frame, the stent support having a proximal end, a proximal portion, a medial portion, a distal portion, and a distal end, an interior area, a longitudinal axis extending from the proximal end to the distal end, and a circumference, wherein the proximal end comprises a crown of a plurality of free peaks pointing in the proximal direction, and the distal end comprises a crown of a plurality of free peaks pointing in the distal direction, and wherein the tubular stent support comprises a plurality of adjacent rows of interconnected diamond-shaped cell structures extending between the proximal end and distal end; the prosthetic heart valve also comprises (ii) a valve structure having a plurality of valve leaflets, i.e. at least two, preferably three valve leaflets, a valve skirt, and a plurality of valve commissure points, and wherein the valve is attached within the interior area of the stent support, such, that in the proximal portion the inner surface of the tubular stent support is lined with the valve forming a sealing zone, that the valve, in a region between the distal end and the medial portion, is fixed to the stent support via the valve commissure points, and that the stent support has, in a region between the distal end and the medial portion, a valve-free portion. Further, the distal end of the stent support, in its crown, has only three free peaks pointing in the distal direction, wherein each of the three peaks pointing in the distal direction has a connecting wire extension structure, the connecting wire extension structure having a first wire section substantially parallel to the longitudinal axis and having a generally longitudinal shape extending from the distal in the proximal direction, and a second wire section at least a portion of which extends in a direction perpendicular to the longitudinal axis.

The prosthetic heart valve according to the invention is also particularly suited for being loaded and introduced into the heart via a loading and deployment system adapted for the prosthetic heart valve. The particular shape of the prosthesis in connection with the connecting wire extension structure at the distal end of the prosthetic heart valve according to the invention allows for an easy and precise loading of the prosthesis onto/in the deployment system as well as for a precise deployment at the site of interest.

With the prosthetic heart valve and its deployment system, a continuous blood flow during deployment of the prosthetic heart valve is guaranteed. Via the three connecting wire extension structures, the distal end of the prosthetic heart valve can be securely fixed in the catheter tip of a deployment system.

With the secure attachment of the distal end in the tip of a deployment system, and with the possibility to separately release the distal end of the prosthetic heart valve—by moving the tip—and the proximal end of the prosthetic heart valve—by not fully retracting the sheath compressing the prosthetic heart valve, a balloon-like deployment can be achieved. This partial release of the prosthetic heart valve is needed, since only with the partial, balloon-like expansion of the prosthetic heart valve the dimension and placement of it and its intended location can be assessed without compromising the blood flow.

Thus, with the special features of the prosthetic heart valve according to the invention, a secure and releasable attachment onto the holding and placing system is achieved, while at the same time, after release of the prosthetic heart valve at the desired location, a secure placement within the vessel is guaranteed. The special design and interacting of the features of the prosthetic heart valve according to the invention provide for a heart valve, which immediately after placement takes over the functions of the natural valve that is to be replaced.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Accordingly, when presently used, the term "distal direction" designates the direction the distal end of the prosthetic heart valve is pointing, and the "proximal direction" the direction the proximal end of the prosthetic heart valve is pointing.

The connecting wire extension structure has, according to the invention, a first wire section substantially parallel to the longitudinal axis and having a generally longitudinal shape extending from the distal in the proximal direction, and a second section at least a portion of which extends in a direction generally perpendicular to the longitudinal axis. The term "generally" as used herein means within 15 degrees parallel or perpendicular, respectively, and also encompasses structures being parallel or nearly parallel, or perpendicular or nearly perpendicular. In particular, in respect of the second section at least a portion of which extends in a direction generally perpendicular to the longitudinal axis, embodiments are encompassed that have a second section that represents a longitudinal wire section generally perpendicular to the longitudinal axis, as well as embodiments that have a second section that has a substantially round or oval or square shape, whereby a portion of the round or oval shape extends perpendicular to the longitudinal axis.

Thus, and according to one embodiment, the second section has a shape that is selected from substantially round, oval, square or longitudinal. According to the invention, these shapes also encompass shapes that are round, oval, square or longitudinal.

Accordingly, in the embodiment with a round or oval shape of the second section, at least a portion of the round/oval/square/longitudinal shape extends in a direction perpendicular to the longitudinal axis, and another portion of the second section extends in the longitudinal direction.

According to a preferred embodiment, the connecting wire extension structure having a first wire section substantially parallel to the longitudinal axis and having a generally longitudinal shape extending from the distal in the proximal direction, and a second wire section at least a portion of which extends in a direction perpendicular to the longitudinal axis, is generally T-shaped.

Also, as used herein, and as generally understood, the term "T-shaped" means any form or structure of an extension of the peaks of a stent support's crown, and, as a consequence of a diamond-shaped cell, that resembles the letter "T", i.e. a structure, where a first bar- or rod-like first (wire) structure or section having a first end and a second end has, on its one end, perpendicularly arranged another second bar- or rod-like (wire) structure or section, which second bar- or rod-like structure can be shorter than the first bar-like (wire) structure.

Accordingly, the "T-shaped wire extension structure" of the prosthetic heart valve according to the invention, points in/towards the distal direction, whereby the perpendicularly arranged second bar-like (wire) structure represents the outmost or ultimate end, and whereby the first bar-like first (wire) structure, being connected via its first end with the perpendicular arranged second bar-like (wire) structure, is, via its second end, arranged or mounted to the stent support, or rather to the crown at the distal end of the stent support/prosthetic heart valve. However, it will be apparent from the present disclosure, that the "bar-like" structure does not necessarily have to be a uniform cylindrical form or shape, but may have portions with larger or smaller diameters. Further, the second bar-like structure being perpendicularly arranged on the first end of the first bar-like structure, may be slightly bent.

Accordingly, and according to one aspect of the prosthetic heart valve according to the invention, the connecting wire extension structure has a first wire section with a first end and a second end, which the first wire section is substantially parallel to the longitudinal axis of the stent support, and a second wire section, which the second wire section has at least a portion which is substantially parallel to the circumference of the stent support and which the second wire section is formed at the second end of the first wire section.

According to another embodiment, the connecting wire extension structure has a second wire section that has a shape that is selected from round, oval, or square.

Presently, "at least a portion" in respect of the second wire section is meant to designate wire sections which are either completely, i.e. all portions of the second wire section, formed perpendicular to the longitudinal axis, or which second wire sections have also portions extending, e.g. in the longitudinal axis of the stent support. E.g., a round or oval or square second wire section will always have portions extending in a direction perpendicular to the longitudinal axis of the stent support, as well as portions which are parallel to the longitudinal axis of the stent support.

The wire frame of the stent support is preferably formed from a shape memory material such as a nickel titanium alloy (e.g., Nitinol) or a very high-tensile material that will expand from its compressed state to its original state after removal of external forces. With this material, the support structure is self-expandable from a contracted state to an expanded state, such as by the application of heat, energy, and the like, or by the removal of external forces (e.g., compressive forces). This support structure can be repeatedly compressed and re-expanded without damaging the structure of the stent support. In addition, the support structure of such an embodiment may be laser cut from a single piece of material or may be assembled from a number of different components. For these types of prosthetic heart valves having a stent support, one example of a delivery system that can be used includes a catheter with a retractable sheath that covers the prosthetic heart valve until it is to be deployed, at which point the sheath can be retracted to allow the stent support and, thus, the prosthetic heart valve as such, to expand. Alternatively, the prosthetic heart valve of the invention can be implanted using conventional surgical techniques and/or minimally invasive surgical procedures. In such cases, the prosthetic heart valves of the invention can advantageously require relatively few or no sutures to secure the stent to an anatomical location within the patient.

The prosthetic heart valve is preferably a prosthetic aortic valve and is intended for replacing or supporting the native diseased aortic valve.

The heart has four valves ensuring that blood does not flow in the wrong direction, e.g. that the blood does not flow back from the ventricles into the corresponding atria. The valve between the left atrium and the left ventricle is the mitral valve, the valve between the right atrium and the right ventricle is the tricuspid valve, and the pulmonary valve is at the opening of pulmonary artery. The aortic valve is a one-way valve between the heart and the aorta, the main artery from the heart that distributes oxygen-rich blood to the body. The aortic valve has normally three small flaps or leaflets that open widely and close securely to regulate blood flow, allowing blood to flow from the heart to the aorta and preventing blood from flowing backwards into the heart. Aortic valve stenosis occurs when calcium is deposited on the valve leaflets, limiting their mobility, and, limiting or blocking the blood flow.

The valve structure as claimed and described comprises a plurality of valve leaflets, a valve skirt portion and valve commissure points or poles; the valve skirt portion represents an area of the valve structure that is used for connecting the valve structure to the stent support, for example, by means of sutures.

The leaflets of the valve structure move to open and close in response to the differential pressure induced by the pumping motions of the heart. Normally, the mitral valve has two leaflets and the tricuspid valve has at least two, preferably three leaflets. The aortic and pulmonary valves normally have at least two, preferably three leaflets, which are also often referred to as "cusps" because of their half-moon like appearance. In the present disclosure, the terms "leaflet" and "cusps" have the same meaning.

The valve leaflets of the prosthetic heart valve according to the invention consist of natural tissue or synthetic material and can switch from an opened position for opening the patient's heart chamber to a closed position for closing the patient's heart chamber.

The valve skirt portion of the valve structure as presently described and as generally understood designates the portion of the valve structure extending from the valve leaflets and towards the proximal direction. The valve leaflets may be integrally formed with the valve skirt portion, e.g. a single piece of pericardium may be used for forming the valve structure. Alternatively, the valve leaflets and the valve skirt may not be integral, and the valve leaflets and the valve skirt can be made of several pieces and of different materials.

Accordingly, the skirt portion consists of natural tissue or synthetic material and is used for mounting of the valve structure to the stent support, thus forming a sealing area in that region. The skirt portion can have different lengths, and preferably extends from the junction towards the very end of the proximal end of the prosthetic heart valve, and the portion is used as a conforming skirt that improves sealing to the aortic root.

The expression "natural tissue" as used herein means naturally occurring tissue, i.e. biological tissue obtained from the patient, from another human donor (homografts), or from a nonhuman animal (xenografts). The expression also covers tissues fabricated by tissue engineering, e.g. from combinations of engineered extracellular matrices ("scaffolds"), cells, and biologically active molecules.

The valve structure of the prosthetic heart valve according to the invention may accordingly either comprises xenografts/homografts or synthetic, nonbiological, materials. Homografts are either human donor valves, e.g., heart valves, or replacements made of human tissue, e.g., pericardial tissue, whereas xenografts describe valves received from animals, e.g., heart valves, or made of animal tissue, e.g., pericardial tissue, typically porcine or bovine.

In a preferred embodiment, the prosthetic heart valve comprises bovine pericardium.

According to a preferred embodiment, the prosthetic heart valve, at its distal end, comprises three substantially V- or U-shaped openings in its circumference which openings open towards the distal end of the stent support. "Substantially" as used herein, i.e. throughout the present invention, and in particular with respect to V- or U-shaped means to designate the approximate shape or design of the openings, which, in the present invention, resemble the shape of the letter V or U. Slight derivations of these shapes are possible, which, however, still resemble the letters V or U, i.e. are substantially V- or U-shaped.

According to a preferred embodiment of the prosthetic heart valve of the invention, a diamond-shaped cell structure is formed of two intersection points that are spaced from each other along the longitudinal axis of the stent support, forming the peaks of one row, and of two intersection points that are spaced from each other relative to the circumference of the stent support, wherein the last row at the distal end comprises only three diamond-shaped cell structures, which are spaced from each other around the circumference of stent support, such, that they do not touch each other.

By the provision of only three diamond-shaped cells, each of which has one peak pointing in the distal direction, the overall stent material at the distal end of the stent support is largely reduced thus facilitating the attachment or fixation of the distal end of the stent support within a loading structure. The connecting wire extension structure of the three peaks of the last row match the loading's system engagement means and the stent support can, thus, easily be loaded and compressed for deployment in a heart of a patient.

According to another preferred embodiment of the prosthetic heart valve according to the invention, the penultimate row at the distal end, i.e. the row adjacent to the last row at the distal end, comprises more diamond-shaped cell structures than the last row of the distal end, wherein some of the diamond-shaped cell structures of the penultimate row are spaced from each other around the circumference of the stent support, and wherein some of the diamond-shaped cell structures of the penultimate row touch each other.

Also, according to another preferred embodiment of the prosthetic heart valve according to the invention, the penultimate row at the distal end, being adjacent to the last row at the distal end, comprises six diamond-shaped cell structures, wherein two cell structures, respectively, of the penultimate row touch each other, thus forming cell structure pairs, wherein the cell structure pairs of the penultimate row are spaced from each other around the circumference of the stent support.

According to a refinement of the prosthetic heart valve according to the invention, the row adjacent in proximal direction to the penultimate row of the distal end comprises more diamond-shaped cell structures than the penultimate row at the distal end.

These embodiments render the overall form of the distal end such, that due to the reduced number of diamond-shaped cells, wherein the reduction increases towards the distal, end, the circumference of the tubular form of the prosthetic heart valve has alternating areas with and without a wire frame, thus forming three "tail"-like wire frame endings at the distal end.

While according to one embodiment of the prosthetic heart valve according to the invention the tubular form of the stent support has, along its longitudinal axis, a generally uniform diameter, in others embodiments the prosthetic heart valve may also have, along its longitudinal axis, different or at least two different diameters.

Thus, according to another embodiment of the prosthetic heart valve according to the invention, the tubular form of the stent support in the valve-free portion, has a diameter that is reduced compared to the remaining tubular shape of the stent support.

According to one aspect of the invention, the prosthetic heart valve has its largest diameter at the proximal end compared to the remaining tubular shape of the prosthetic heart valve.

It is also preferred if the commissure poles are flexible in order that they move inward during the valve closure, thus transferring the stress created by the pressure gradient, from the pericardium, which, as a biological material has unpredictable behaviour, to the stent support, which, as a synthetic material, has isotropic characteristics and predictable mechanical behaviour. Advantageously, this will protect the pericardium tissue and, thus, increase the expected useful life of the prosthetic heart valve.

It will also be apparent to those skilled in the art that the length of the tubular prosthetic heart valve will depend on the valve to be replaced, on the patient, and on the overall patient's vessel's condition.

According to another embodiment of the prosthetic heart valve according to the invention radiopaque markers are provided in the medial portion of the stent support, i.e. in the transition area between the leaflets of the valve and the valve skirt portion. This allows the user in each state of deployment a precise knowledge of the valve/leaflet level. It is preferred if the radiopaque markers are made of or comprise a material that is selected from gold, platinum alloys tantalum or other radiopaque materials. Also, the form of the markers can be any form, such as, round, square, oval, etc. The markers are preferably attached to the stent support via riveting, bonding or other attachment/mounting means.

Presently, and throughout the invention and as generally understood, the term "substantially" in connection with an accompanying adjective used herein shall also comprise not only the exact definition of the adjective, such as, e.g. parallel, but also slight and fine deviances therefrom, but which still fall under the general and overall definition of the adjective.

The prosthetic heart valve according to the invention is particularly suited for employment with the deployment system according to the invention. The prosthetic heart valve and the deployment system are interoperating such, that when the deployment system has been actuated to bring the prosthetic heart valve loaded thereupon in a balloon-like release state, the native valve can still be passed which allows for a very precise positioning. Also, the prosthesis is fully reloadable, since in case its removal or replacement should be necessary, it can be retracted back into the sheath.

Further, once the distal end of the prosthetic heart valve, which is, in its loaded state, fixed within the tip, is released, the tip can be moved within the expanded end of the prosthesis. As a consequence, the tip is prevented from interfering with the valve material which might otherwise lead to a damaging of the prosthetic heart valve.

Also, with the very specific design of the prosthetic heart valve, formation of a "parachute", which might obstruct the blood flow, is avoided, since the prosthesis can be positioned exactly at the desired site and upon deployment of the proximal end the prosthetic heart valve is fully functioning.

According to another aspect of the prosthetic heart valve according to the invention the prosthetic heart valve, in a region where the medial portion transitions into the proximal portion comprises a portion that is concave with respect to the longitudinal axis of the stent support.

Presently, and as generally understood, the expression "concave" as used herein means a form that is inwardly curved as opposite to outwardly curved, i.e. as opposite to convex. Thus, the wall or the wire frame of the stent support or the prosthetic heart valve as such in this area is inwardly curved, and not only on one side, but over its whole circumference. The degree of the inwardly curving may be only slight.

This embodiment has the advantage that via the concave form in this region, i.e. the sealing portion that is lined with the valve structure and that is to be placed at the location where the natural valve lies, the calcium packages present mostly in the native valve leaflets suffering of calcific stenosis can be accommodated better. Accordingly, the concave shape is meant to fix safely around the anatomical structure of the calcified native, e.g., aortic valve.

The invention also concerns a method for releasing the prosthetic heart valve according to the invention loaded on a deployment system, comprising a catheter, a shaft, a sheath, a tip, and an actuating mechanism, the method comprising the steps of:

providing a deployment system having an expandable prosthetic heart valve according to the invention loaded thereon, actuating the actuating mechanism of the deployment system in order to stepwise retract the sheath, thus releasing a medial portion of the prosthetic heart valve, whereby the distal end of the prosthetic heart valve remains fixed within the tip, and the proximal end of the prosthetic heart valve remains fixed in the distal end of the shaft, thereby permitting a balloon-like expansion of the prosthetic heart valve, moving the tip and, thus, releasing the distal end of the prosthetic heart valve, and fully retracting the sheath and fully deploying and releasing the expandable prosthetic heart valve.

With the method described herein, a precise placement of the prosthetic heart valve is possible. Also, employing the method of the invention allows the practitioner or surgeon to carefully place and even re-place the prosthetic heart valve, without being under time pressure for timely positioning the prosthetic heart valve in order not to obstruct blood flow. Since with the method according to the invention, a balloon-like intermediate step of deploying the prosthesis is generated, flow of blood past the prosthetic heart valve is guaranteed, thus providing time for a deliberate deployment of the prosthetic heart valve. Further, with the method according to the invention, flaring of the released end of the prosthesis is prohibited.

According to a refinement of the invention, the method further comprises, after the providing-step, the step of:

positioning the deployment system such, that the prosthetic heart valve is in the area of the cardiac valve to be replaced by the prosthetic heart valve.

It is understood that the features described hereinabove and those still to be described below fall within the scope of the present invention not only in the respectively specified combinations, but also in different combinations or on their own, such, that the disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Preferred embodiments are shown in the Figures and are described in further detail herein below.

DETAILED DESCRIPTION OF THE FIGURE

Figure 1A:
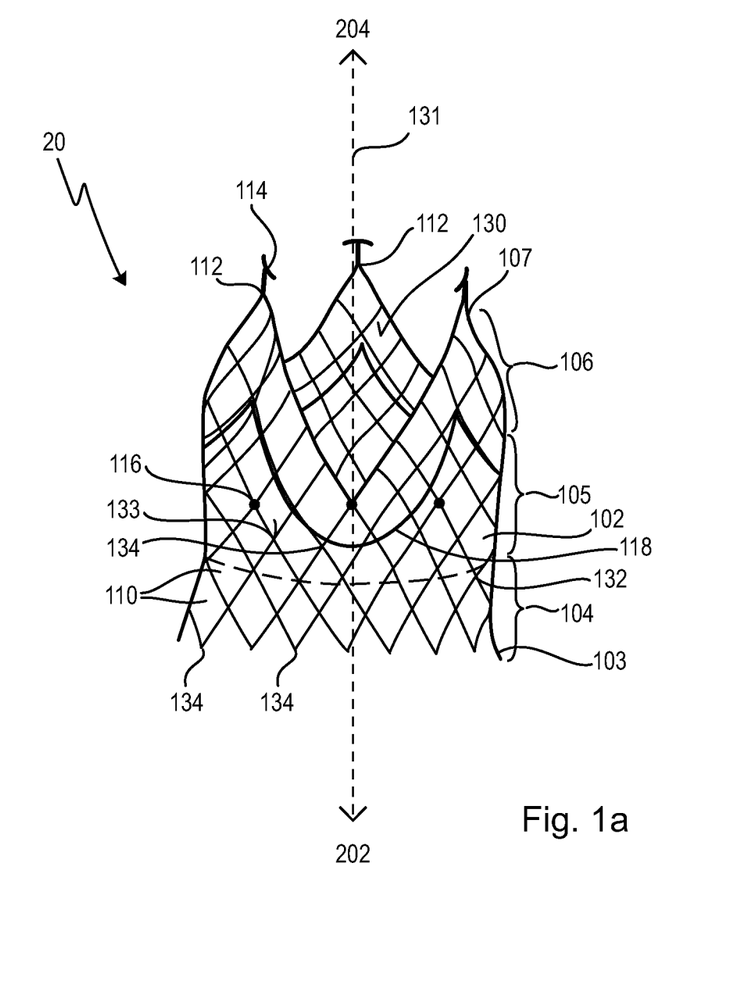
FIGS. 1A, 1B, and 1C show an exemplary embodiment of the prosthetic heart valve according to the invention, whereby FIGS. 1A, 1B and 1C each show the same embodiment; due to clarity reasons, in the FIGS. 1A, 1B and 1C not every feature described in the following description is shown in each of 1A, 1B and 1C, but rather the respective feature discussed for the respective FIGURE.
Figure 1B:
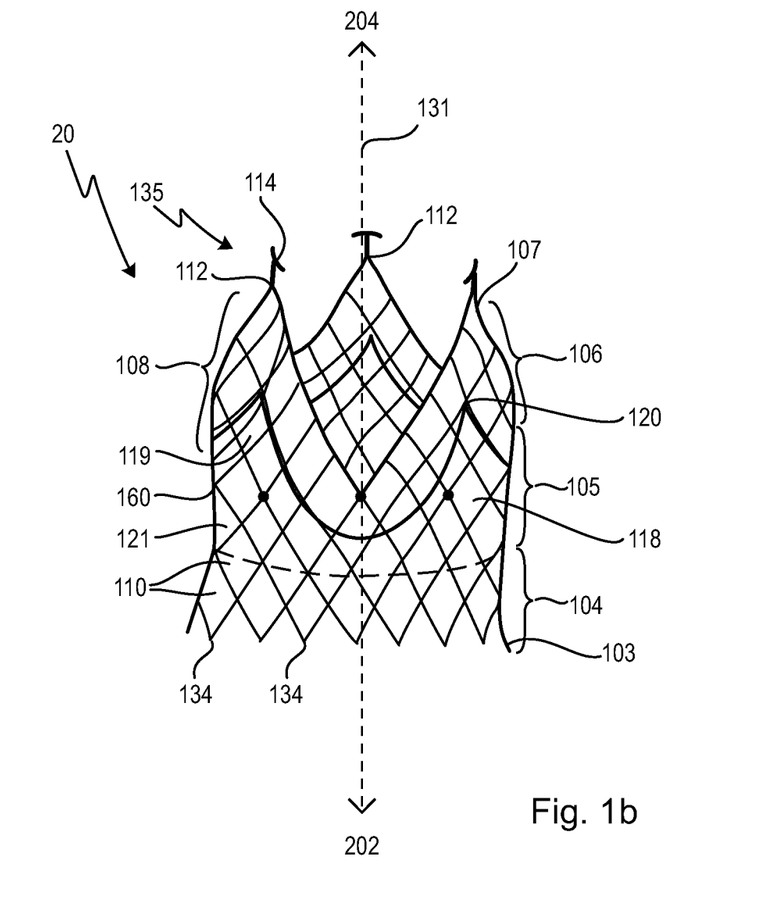
Figure 1C:
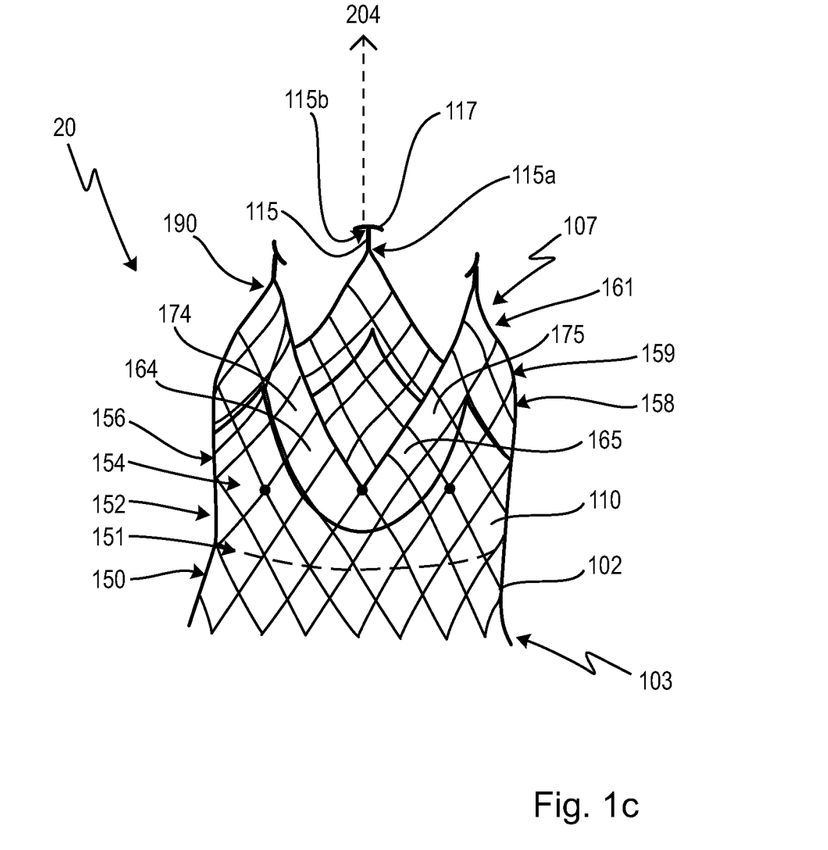

In the following, the exemplary embodiment of the prosthetic heart valve as shown in FIGS. 1A, 1B and 1C is described, wherein the reference numbers of the features of the embodiment are the same for each of FIGS. 1A, 1B and 1C. It goes without saying that the features described and designated in each of FIGS. 1A, 1B and 1C are the same as for the respective other FIGURE.

The prosthetic heart valve 20 has an expandable generally tubular stent support 102 forming a wire frame. The stent support 102 has a proximal end 103, a proximal portion 104, a medial portion 105, a distal portion 106, and a distal end 107. The stent support 102 also has an interior area 130, a longitudinal axis 131 extending from the proximal end 103 to the distal end 107, and a circumference 132.

The proximal end 103 and the distal end 107 each comprises a crown with a plurality of free peaks 134, 112. At the proximal end 103, the peaks 134 are pointing in a proximal direction 202, at the distal end, the peaks 112 are pointing in the distal direction 204. As mentioned above, the "distal direction" designates the direction in which the distal end 107 of the prosthetic heart valve 20 is pointing, and the "proximal direction" designates the direction in which the proximal end 103 of the prosthetic heart valve is pointing.

As can be seen from FIG. 1, the tubular stent support further comprises a plurality of adjacent rows of interconnected diamond-shaped cell structures 110 extending between the proximal end 103 and distal end 107.

The diamond shaped cell structures 110 may be, e.g. laser-cut or formed by interweaving or braiding metal, preferably Nitinol, wires.

As depicted in FIG. 1, the diamond-shaped cell structures 110 are arranged in adjacent rows, where each of the diamond cell structures 110 is defined by a series of wires or wire segments of the wire frame formed by stent support 102: Due to the diamond shape of these cell structures 110, at least one "peak" of each diamond-shaped cell structure 110 of one row coincides with a "valley" created by two circumferentially adjacent diamond-shaped cell structures 110 in an adjacent row. Accordingly, a single row comprises multiple diamond-shaped cell structures 110 that are circumferentially adjacent to each other around the stent support 102. Also, accordingly, a row of diamond-shaped cell structures 110 adjacent to another row comprising multiple diamond-shaped structures 110, herein designated as "adjacent row", is a row that is located closest to, or interconnecting with, another row of diamond cell structures 110 along the longitudinal direction of the stent support 102.

Further, a "diamond" shaped cell structure as used herein is intended to generally mean the wire-segmented, four-sided cell shapes 110 in FIG. 1 which comprise intersection points where two adjacent wires or wire segments meet. As shown in FIG. 1, each diamond cell structure 110 has four intersection points, i.e. two intersection points that are spaced from each other along the longitudinal axis 131 of the stent support 102, which are referred to as "peaks" 133, 134 of one row (or which can be referred to as the "valleys" of an adjacent row). The diamond cell structures 110 further include two intersection points that are spaced from each other relative to the circumference 132 of the stent support 102.

At the distal end 107 the stent support 102 comprises a crown 135 having three free peaks 112, i.e. three diamond-shaped cells 110 at the distal end 107 each have a free peak 112. Accordingly, the term "free" when used in connection with "peak" is meant to designate a peak or intersection point that is not connected or adjacent to or forming edges with another cell structure 110. As can also be seen in FIG. 1, all three of the free peaks 112 of the diamond shaped expandable cell structures 110 pointing in the distal direction have a connecting wire extension structure 114. In the embodiment shown, the connecting wire extension structure is T-shaped.

The three connecting wire extension structures 114 present on the three free peaks 134 are used for attachment/connection to a delivery system, and are specifically configured to allow for removable attachment/connection of the stent support 102 relative to the delivery system.

The embodiment of the prosthetic heart valve 10 as shown in the figures has a connecting wire extension structure 114 that is generally T-shaped. Presently, and as mentioned above, with the expression "T-shaped" any form or design of the free peak 112 of a cell structure 110 is meant, which has the shape of the letter "T".

As can be seen in FIG. 1, in particular in FIG. 1c, the connecting wire extension structure 114 comprises a first wire extension section 115 that runs substantially parallel to the longitudinal axis 131 of the stent support 102, and another, a second wire extension section 117 that is substantially parallel to the circumference 132 of the stent support 102. As such, the second wire extension section 117 can have any other form at least a portion of which is perpendicular to the longitudinal axis 131 of stent support 102, e.g. round or oval, or square. First and second wire extension structure 115, 117, together, form the connecting wire extension structure adapted for engaging with respective engaging elements of the deployment system (not shown).

Further, and as indicated in FIG. 1c, the first wire extension structure 115 has a first end 115a and a second end 115b. With its first end 115a, the connecting wire extension structure is attached to (or formed integrally with) one of the three free peaks/ends of 112 of stent support 102, while the other, a second end 115b, is coupled with/attached to or formed integrally with the second wire extension section 117.

Further, as can be seen from FIG. 1, the medial portion 105 of the stent support 102 carries radiopaque markers 116, thus facilitating the orientation and placement of the prosthetic heart valve 20. In addition, the size of the cell structures 110 in the distal portion 106 of the stent support 102 is greater than the size of the cell structures 110 in the proximal portion 104 of the stent support 102.

As can also be seen in FIGS. 1A, 1B and 1C, and with particular reference to FIG. 1B, the prosthetic heart valve 20 also comprises a valve structure 118 having a plurality (i.e. three) of valve leaflets 119, and a plurality of valve commissure points 120. The valve structure 118 also comprises a valve skirt 121, which is attached to the stent support 102, such, that the valve structure 118 partially lines the inner area of the stent support 102, thus, forming, in the proximal portion 104, a sealing zone, wherein the inner area of the tubular stent support 102 is lined with the valve skirt 121.

As mentioned above, the material of the stent support 102 is preferably made from nitinol or any other metal with shape-memory characteristics. The valve may be a donor valve, e.g. a valve from a mammal, or an artificial valve.

Further, in the prosthetic heart valve 20 according to the invention, the valve structure 118 is, in a region 108 between the distal end 107 and the medial portion 105, and preferably in the distal portion 106 of the stent support 102, fixed to the stent support 102, namely via its commissure points 120. The stent support 102 has further, in a region 108 between the distal end 107 and the medial portion 105, a valve-free portion.

As mentioned above the commissure poles/points 120 are flexible and move inward during the closure of the valve.

Further, FIGS. 1A, 1B and 1C show that the prosthetic heart valve 20, in the region where the medial portion 105 transitions into the proximal portion 104, comprises a concave portion 160, i.e. a portion or section 160 where the tubular stent support 102 has a concave wall, i.e. a wall that is inwardly (relative to the tube-like structure) curved. This feature allows to better accommodate the calcium packages generally present in the native valve leaflets.

The concave form of portion 160 can be achieved, e.g., by providing the stent support 102 in this portion with lesser expansion forces of the diamond-shaped cell structures 110 than diamond-shaped cell structures in other regions of the stent support 102. The lesser expansion force may be achieved by, e.g., cutting a stent structure from a nitinol tube having a certain length and thickness; in order to form the desired stent structure 102, the structure cut from the tube is thermally expanded by means of special tool mandrels until the desired diameter is reached; by using tool mandrels with different diameters, it is, thus, possible to generate areas or portions of the tube/stent structure 102 having different diameters.

With particular reference again to FIG. 1C, stent support 102 includes a series of adjacent rows of diamond-shaped cell structures 110. In particular, stent support 102 includes a first row 150 of such cell structures at the proximal end 103 of the stent support 102, which is, in longitudinal direction and towards the distal end, followed or adjacent to row 151 of diamond-shaped cell structures 110. Row 151 preferably comprises as many cell structures 110 as row 150; each of the structures of row 151 shares at least a portion of two wire segments with cell structures 110 of row 150. Row 151 is, in distal direction, followed by row 152 which preferably comprises as many cell structures 110 as row 151; each of the structures of row 152 shares at least a portion of two wire segments with cell structures 110 of row 151.

The next row 154—being adjacent to row 152—again includes the same number of diamond-shaped cell structures 110 as rows 150 and 152.

Row 156, adjacent to row 154, then comprises less diamond-shaped cell structures 110, and, as a consequence, row 156 comprises cell structures 110 that are regarded as being neighbored in the same row that that do not touch each other; in other words, they are spaced from each other around the circumference of stent support 102. As a consequence, a "gap" is formed between cells 164 and 165 of row 156.

Further, what can also be taken from FIG. 1, row 156 not only comprises one gap, but three gaps, which are separated or spaced from each other in periodic distances: this is due to the fact that, also in periodic distances, row 156 is "missing" three diamond-shaped cell structures 110.

Further, row 158, being adjacent to row 156 towards the distal end 107 of the stent support 102, again comprises less diamond-shaped cell structures 110 than row 156, which feature, as a consequence, enlarges the gap between the cells 174, 175 of row 158 compared to the gap of row 156. Further, as can also be seen in FIG. 1, the gap present in row 158 is adjacent to the gap of row 156, thus providing—together with the adjacent, subsequently larger getting gaps in the adjacent rows 159 and 161—a terminal V-shaped opening in the circumference of stent support 102.

As already explained for row 156, each row 158, 159 and 161 also comprise not only one gap, but three gaps, which are separated or spaced from each other in periodic distances around the circumference of stent support 102 and which are adjacent to the gap in the previous, i.e. to the more proximal, row, thus enlarging the V or U-shaped openings in the wall or circumference 132 of stent support 102.

The last row 190 at the distal end 107 of stent support 102 comprises, as can be seen from FIGS. 1A, 1B and 1C, only, i.e. solely or exclusively, three diamond-shaped cell structures 110, the peaks of which, respectively, form the distal crown 135 carrying the connecting wire extension structures 114.

As such, the stent support 102 of the prosthetic heart valve 20 has three V- or U-shaped openings which open towards the distal end 107. Thus, the three "V"s or "U"s formed in the circumference 132 of stent support towards the distal end 107 each represent a terminal opening in the circumference 132 of prosthetic heart valve 20 which are separated from one another through tail-like structures formed by the continuously reduced cell structures 110 in rows 156, 158, 159 and 160.

Valve structure 118 is secured via its commissure points or poles 120 to the stent support 102, such, that the commissure points 120 are located in the region of the tail-like structures.

What can also be seen from FIGS. 1A, 1B and 10 is that in the distal portion 106 of the stent support 102 has a diameter that is smaller than the diameter of the stent support 102 in other stent support portions.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not restricted except in light of the attached claims and their equivalents.

The invention claimed is:

1. A prosthetic heart valve for replacement of a native valve of a patient, wherein the prosthetic heart valve comprises:
    an expandable generally tubular stent support forming a wire frame and having proximal end, a proximal portion, a medial portion, a distal portion, and a distal end, an interior area, a longitudinal axis extending from the proximal end to the distal end, and a circumference, wherein the proximal end and the distal end each comprises a crown of a plurality of free peaks pointing in the proximal and distal direction, respectively, and wherein the tubular stent support comprises a plurality of adjacent rows of interconnected diamond-shaped cell structures extending between the proximal end and distal end, wherein a diamond-shaped cell structure is formed of two intersection points that are spaced from each other along the longitudinal axis of the stent support, forming the peaks of one row, and of two intersection points that are spaced from each other relative to the circumference of the stent support, wherein a last row at the distal end comprises only three diamond-shaped cell structures, which are spaced from each other around the circumference of the stent support, such, that they do not touch each other; and
    a valve structure having a plurality of valve leaflets, a valve skirt, and a plurality of valve commissure points, and wherein the valve structure is attached within the interior area of the stent support, such that in the proximal portion the inner surface of the tubular stent support is lined with the valve structure forming a sealing zone, such that the valve structure, in a region between the distal end and the medial portion, is fixed to the stent support via the commissure points, and such that the stent support has, in a region between the distal end and the medial portion, a valve-free portion;
    wherein the distal end of the stent support, in its crown, has only three free peaks all of which peaks have a connecting wire extension structure, the connecting wire extension structure having a first wire section substantially parallel to the longitudinal axis and having a generally longitudinal shape extending from the distal end in the proximal direction, and having a second wire section at least a portion of which extends in a direction perpendicular to the longitudinal axis.

2. The prosthetic heart valve of claim 1, wherein the prosthetic heart valve at its distal end comprises three V- or U-shaped openings in its circumference which the V- or U-shaped openings open towards the distal end of the stent support.

3. The prosthetic heart valve of claim 1, wherein a row adjacent to a last row at the proximal end comprises more diamond-shaped cell structures than the last row of the distal end, wherein some of the cell structures are spaced from each other around the circumference of the stent support, and wherein some of the cell structures touch each other.

4. The prosthetic heart valve of claim 3, wherein a penultimate row at the distal end, being adjacent to the last row at the distal end, comprises six diamond-shaped cell structures, wherein two cell structures touch each other, respectively, thus forming cell structure pairs, wherein the cell structure pairs are spaced from each other around the circumference of the stent support.

5. The prosthetic heart valve of claim 1, wherein a row adjacent in proximal direction to the penultimate row of the distal end comprises more diamond-shaped cell structures than the penultimate row at the distal end.

6. The prosthetic heart valve of claim 1, wherein in the medial portion of the stent support radiopaque markers are provided.

7. The prosthetic heart valve of claim 1, wherein at the distal end, the tubular shape of the stent support in the valve-free portion has a diameter that is reduced compared to the remaining tubular shape of the stent support.

8. The prosthetic heart valve of claim 1, wherein at a fixation site of the commissure points of the valve structure to the stent support, the tubular shape of the stent support is flexible.

9. The prosthetic heart valve of claim 1, wherein the connecting wire extension structure has a first wire section with a first end and a second end and being substantially parallel to the longitudinal axis of the stent support, and a second wire section located at the second end of the first wire section.

10. The prosthetic heart valve of claim 1, wherein the second wire section has a shape that is selected from substantially round, oval, square, or longitudinal.

11. The prosthetic heart valve of claim 1, wherein the connecting wire extension structure is T-shaped.

12. The prosthetic heart valve of claim 1, wherein in the area where the medial portion transitions into the proximal portion the prosthetic heart valve comprises a region that is concave with respect to the longitudinal axis of the stent support.

* * * * *